United States Patent

Esteve-Subirana

[11] 4,115,648
[45] Sep. 19, 1978

[54] 2,5-DIHYDROXY BENZENE SULFONIC ACID MONO ESTERS

[75] Inventor: Antonio Esteve-Subirana, Barcelona, Spain

[73] Assignee: Laboratorios del Dr. Esteve, S.A., Barcelona, Spain

[21] Appl. No.: 626,024

[22] Filed: Oct. 28, 1975

Related U.S. Application Data

[60] Division of Ser. No. 505,934, Sep. 13, 1974, Pat. No. 3,954,767, which is a continuation-in-part of Ser. No. 360,394, May 14, 1973, Pat. No. 3,876,651.

[51] Int. Cl.$^2$ .................. C07C 143/68; C07D 295/00
[52] U.S. Cl. ............................... 544/110; 260/456 P
[58] Field of Search .................... 260/247.1 E, 456 P; 544/110

[56] References Cited

U.S. PATENT DOCUMENTS 3,354,201  11/1967  Esteve-Subirana ............. 260/501.21

OTHER PUBLICATIONS

Marmo "Chem Abstracts" vol. 75, (1971) No. 87001w.
Burger "Medicinal Chemistry" 2nd ed. (1960) p. 42.

Primary Examiner—Natalie Trousof
Assistant Examiner—R. W. Ramsuer
Attorney, Agent, or Firm—Henry L. Brinks

[57] ABSTRACT

Mono- and diesters of 2,5-dihydroxy benzene sulfonic acid are represented by one of the following formulae:

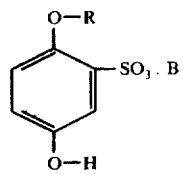

I

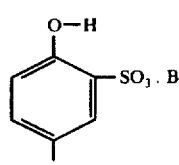

II

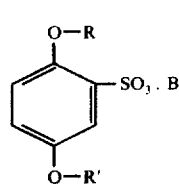

III wherein R and R' can be identical or different and represent an alkanyl, arylalkanoyl, aryloxyalkanoyl, aryl, alkanesulfonyl, arenesulfonyl, alkylarenesulfonyl or arylalkanesulfonyl radical, B represents the cation of an alkali metal, alkaline-earth metal of ammonia or an unsubstituted or substituted, open chain or cyclic amine, and are remarkable for their hypocholesterolemic, hypotriglycidemic and hypolipidemic activity.

2 Claims, No Drawings

2,5-DIHYDROXY BENZENE SULFONIC ACID MONO ESTERS

This is a division of co-pending application, Ser. No. 505,934, filed Sept. 13, 1974, by the same inventor as herein, now U.S. Pat. No. 3,954,767 which is a continuation-in-part of my co-pending application Ser. No. 360,394 filed May 14, 1973 now U.S. Pat. No. 3,876,651.

This invention concerns novel 2,5-dihydroxy benzene sulfonic acid mono- and diesters, and a process for preparing them.

These compounds have one of the following formulae:

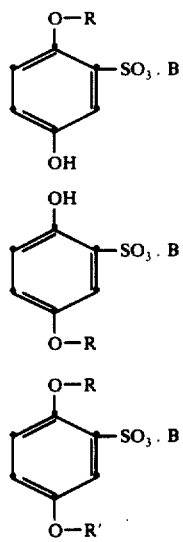

wherein R and R' can be identical or different, and represent an alkanoyl, arylalkanoyl, aryloxyalkanoyl, aroyl, alkanesulfonyl, arenesulfonyl, alkylarensulfonyl or arylalkanesulfonyl radical. On the other hand, B is an alkali metal, an alkaline-earth metal, ammonia or unsubstituted or substituted amine cation, for instance alkanoylamines, alkyl- and aryl-amines, cyclic amines etc.

Compounds having the general formulae I, II and III possess extremely interesting pharmacodynamical properties. Particularly, they show a potent hypocholesterolemic, hypotriglycidemic, and hypolipidemic effect.

According to the invention, the process for preparing compounds having general formulae I, II and III is characterized in that a compound of formula:

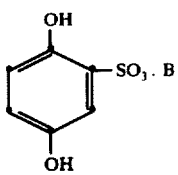

wherein B has the above-defined meaning, is reacted with a halide or an anhydride of the acid of formula R-H, and optionally with an acid of formula R'-H wherein R has the above-defined meaning.

The operation is effected preferably in an aprotic medium, generally a proton acceptor base such as pyridine, picoline, trimethylamine etc., to which may be added an organic solvent inert under the reaction conditions, for instance benzene, toluene, chloroform, diethyl ether, dimethylformamide, etc. Desirably the reaction is effected at a temperature between 20° and −10° C., preferably between 5° and −10° C. It is also possible to effect the reaction at a higher temperature, but then external cooling must be provided, since the reaction is exothermic.

While studying the reaction, one has observed that it can be performed starting from the sulfonic acid in free or salt form, although the yield of the operation is clearly higher when starting from the salt, than when starting from the free acid. It was also noted that the operation develops much better if, in addition to using a salt of the sulfonic acid, pyridine is used as the only solvent; in this way the pyridine salt of the desired compound is obtained with optimum yield. Starting from this pyridine salt, the other desired salts may be obtained by simple displacement.

All the thus obtained compounds can be separated from the reaction mixture in the usual manner, generally by simple filtration, optionally after preliminary decolorizing with charcoal, in the warm solution, and filtering while warm. They are then purified, e.g. by recristallization.

The compounds according to this invention significantly inhibit the increase of plasma chlolesterol, triglycerides and total lipids contents in rats treated with Triton WR-1339 (Friedman M & Byers S. O., J. Exptl. Med., 97, 117, 1953; Garattini S., Morpurgo C., Paoletti P. & Paoletti R., Arzneim.-forsch., 9, 206, 1959; Garattini S., Bizzi L., Grossi E & Vertua R., "Drugs affecting Lipid Metabolism", Elsevier, 1961, p. 144–157). They significantly inhibit too the increase of plasma cholesterol and total lipids in white Leghorn chickens (Tennent D. M., Siegel H., Kuron G. W., Ott W. H. & Mushett C. W., Proc. Soc. Exptl. Biol. Med., 96, 679, 1957). The acute toxicities for the mouse are also very low. The medium lethal dose ($LD_{50}$) for the mouse was determined according to the modified method of Reed and Muench (Reed L. J. & Muench H., Am. J. Hyg., 27, 493, 1938).

Very useful are esters of the general formula:

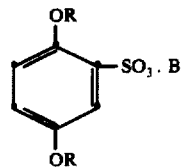

wherein each R residue is hydrogen or the residue of p-toluen sulfonic acid having the formula:

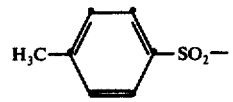

with the proviso that both Rs are not hydrogen simultaneously, and B is hydrogen or the equivalent of an inorganic or organic cation, are particularly desirable.

The salts of piperazine, piperidine, morpholine, diothylamine and sodium are preferred. They can be prepared from the pyridine salt by simple displacement.

The pharmacodynamical properties of the compounds described above are illustrated herebelow by those of piperazine 2,5-dihydroxy benzene sulfonate mono-tosylate, prepared in Example 13 of this invention.

(1) Acute toxicity in the mouse and rat
18 to 25 gr albino mouse.
100 to 150 gr. Sprague-Dawley rats.
The $LD_{50}$ was determined according to the method of Reed and Muench.

Table I

| administration | species | $LD_{50}$(mg/Kg) | fiducial limits (for p = 0,95) |
|---|---|---|---|
| oral | mouse ♂ | >10750 | — |
| oral | mouse ♀ | >10750 | — |
| oral | rat ♂ | >11911 | — |
| oral | rat ♀ | 11911 | (13669 – 10371) |

(2) Hypolipemic action on the rat

The above-mentioned Triton WR-1339 method was selected. The total cholesterol, triglycerides and total lipids were determined in the serum. The results obtained are given in Table II. The amount of Triton WR-1339 administered to the animals was 300 mg/kg. The amount of piperazine 2,5-dihydroxy benzene sulfonate mono-tosylate administered was 2 mMoles/Kg orally. The letter P signifies probability.

Table II

| | Triton | Triton + piperazino 2,5-dihydroxy benzene sulfonate monotosylate |
|---|---|---|
| total cholesterol mg % ml of plasma | 283,3 | 232,3 |
| Δ% with respect to Triton | | −18% |
| P | | 0,0005<P<0,0025 |
| triglycerides mg % ml of plasma | 1122,5 | 639,8 |
| Δ% with respect to Triton | | −43 % |
| P | | P<0,0005 |
| total lipids mg % ml of plasma | 2088,6 | 1211,4 |
| Δ% with respect to Triton | | −42% |
| P | | P<0,0005 |

(3) Hypolipemic action on the chicken

This study was performed with white Leghorn chickens, according to the above-mentioned method. The total cholesterol and the total lipids are determined in the plasma. The results obtained are given in Table III.

Table III

| | check sample | piperazine 2,5-dihydroxy benzene sulfonate monotosylate |
|---|---|---|
| total cholesterol mg % ml of plasma, initial value (a) | 89,1 | 93,1 |
| total cholesterol mg % ml of plasma, final value (b) | 1348,6 | 947,2 |
| $\frac{b}{a} \cdot 100$ | 1514 (X) | 1017 (Y) |
| $\frac{X-Y}{X} \cdot 100$ | | − 33 % |
| P | | 0,0125<P<0,025 |
| total lipids mg % ml of plasma, initial value (a) | 316,3 | 325,2 |
| total lipids mg % ml of plasma, final value (b) | 3401,7 | 2360,8 |
| $\frac{b}{a} \cdot 100$ | 1075 (X) | 726 (Y) |
| $\frac{X-Y}{X} \cdot 100$ | | − 32 % |
| P | | 0,005<P<0,010 |

Very useful too are esters of the general formula:

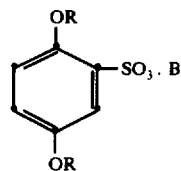

wherein each R residue is hydrogen or the residue of p-chlorophenoxy isobutyric acid having the formula:

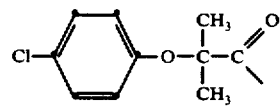

with the proviso that both Rs are not hydrogen simultaneously, and B is hydrogen or the equivalent of an inorganic or organic cation, are particularly desirable.

The salts of magnesium, calcium and piperazine are preferred. They can be prepared simply by neutralizing sulfonic acid, for instance with magnesium or calcium carbonate, or with piperazine which can neutralize one or two molecules of the acid. The latter can be prepared from the pyridine salt, by treating said salt with concentrated sulfuric acid, preferably with approximately 18 N sulfuric acid, in the case of di-esters and mono-esters in the 5-position.

Mono-esterification in 2-position is effected starting from the calcium salt of 2,5-dihydroxy benzene sulfonic acid, according to Example 33; thus the corresponding calcium salt is obtained directly. The magnesium or piperazine salts are prepared by neutralizing the mono-2-O-(p-chloro phenoxy isobutyroyl)-2,5-dihydroxy benzene sulfonic acid, obtained by treating the calcium salt according to Example 33 with approximately 2N sulfuric acid.

The pharmacodynamical properties of the compounds described above are illustrated herebelow by those of the piperazine salt with one mole of the di-O-(p-chloro phenoxy isobutyrate) of 2,5-dihydroxy benzene sulfonic acid, prepared in Example 29 of this invention.

(1) Acute toxicity in the mouse and rat
18 to 25 gr albino mouse.
100 to 150 gr. Sprague-Dawley rats.
The $LD_{50}$ was determined according to the method of Reed and Muench.

Table IV

| administration | species | $LD_{50}$ (mg/Kg) | fiducial limits (for p = 0,95) |
|---|---|---|---|
| oral | mouse ♂ | 11038 | (15502 – 7840) |
| oral | mouse ♀ | 8697 | (12931 – 5826) |
| oral | rat ♂ | 11000 | (12450 – 9713) |
| oral | rat ♀ | 11700 | (13120 – 10420) |

(2) Hypolipemic action on the rat

The above-mentioned Triton WR-1339 method was selected. The total cholesterol, triglycerides and total lipids were determined in the serum. The results obtained are given in Table V. The amount of Triton WR-1339 administered to the animals was 300 mg/Kg. The amount of the piperazine salt with one mole of the di-O-(p-chloro phenoxy isobutyrate) of 2,5-dihydroxy benzene sulfonic acid administered was 1 mMol/Kg orally. The letter P signifies probability.

Table V

|  | Triton | Triton + piperazine of di-O-(p-chloro phenoxy isobutyrate) of 2,5-dihydroxy benzene sulfonic acid |
|---|---|---|
| total cholesterol mg % ml of plasma | 283,3 | 212,5 |
| Δ% with respect to Triton |  | −25 % |
| P |  | 0,0025 < P < 0,005 |
| triglycerides mg % ml of plasma | 1122,5 | 572,5 |
| Δ% with respect to Triton |  | −49 % |
| P |  | 0,005 < P < 0,010 |
| total lipids mg % ml of plasma | 2088,6 | 1503,8 |
| Δ% with respect to Triton |  | −28 % |
| P |  | 0,005 < P < 0,010 |

The following examples illustrate the invention.

EXAMPLE 1

A solution of 29 gr of diethylamine 2,5-dihydroxy benzene sulfonate in 100 ml of pyridine is placed in an erlenmeyer provided with stirring means and a cooling bath, and 10 gr of succinic anhydride are gradually added thereto. Stirring is continued for two hours at room temperature, and the reaction is set aside for 14 hours in a chamber at 60° C. The reaction mixture is poured on to a mixture of ice and concentrated hydrochloric acid, and it is extracted with chloroform. After evaporating the chloroform from the extract, a solid is obtained which is recrystallized in ethanol. Yield: 9.0 gr; melting point: 82° C. It is the monosuccinate of pyridine-2,5-dihydroxy-benzene-sulfonate.

EXAMPLE 2

To a solution of 1 gr of sodium 2,5-dihydroxy benzene sulfonate in 15 ml of pyridine, placed in an erlenmayer provided with stirring means and a cooling bath, 1.2 gr of p-chlorophenoxy isobutyryl chloride are added, stirring is continued for 1 hour, and it is left in a chamber at 60° C. overnight. The reaction mixture is poured on to a mixture of ice and hydrochloric acid, and extracted with chloroform. Finally, 1,2 gr of mono-p-chloro phenoxy isobutyrate of pyridine 2,5-dihydroxy benzene sulfonate, melting point: 114° C., are obtained.

EXAMPLE 3

Into a flask provided with stirring means and a cooling bath, a solution of 26 gr of diethylamine, 2,5-dihydroxy benzene sulfonate in 150 ml of pyridine, is placed, and 30 gr of benzoyl chloride are added gradually. Stirring is continued for 5 hours, and the mixture is poured on to a mixture of ice and concentrated hydrochloric acid. It is left in a refrigerator for 12 hours, and the precipitate obtained is collected on a filter, and recrystallized in methanol. Yield 35 gr; melting point: 235° C. It is the dibenzoate of pyridine 2,5-dihydroxy benzene sulfonate.

EXAMPLE 4

Into a flask provided with stirring and refrigerating means, a solution of 53 gr of diethylamine 2,5-dihydroxy benzene sulfonate in 300 ml of pyridine are placed, and 28 gr of benzoyl chloride are added gradually. Stirring is continued overnight, and the reaction mixture is poured on to a mixture of ice and concentrated hydrochloric acid. 35 gr of the monobenzoate of pyridine 2,5-dihydroxy benzene sulfonate, melting point: 140° C., are obtained.

EXAMPLE 5

A solution of 23 gr of diethylamine 2,5-dihydroxy benzene sulfonate in 150 ml of pyridine are placed in a flask provided with stirring and refrigerating means, and a suspension of 25 gr of nicotinoyl chloride hydrochloride in 50 ml of benzene are slowly added, stirring being continued for 8 hours. The reaction mixture is poured into a mixture of ice and concentrated hydrochloric acid, and 25 gr of pyridine 2,5-dihydroxybenzene sulfonate mono nicotinate, having a melting point of 270° C., are obtained.

EXAMPLE 6

A solution of 29 gr of diethylamine 2,5-dihydroxy benzene sulfonate in 150 ml of pyridine are placed in a flask provided with stirring and refrigerating means, and 28 ml of benzene sulfonyl chloride are gradually added. Stirring is continued for 14 hours, and the reaction mixture is poured on to a mixture of ice and concentrated hydrochloric acid. After recrystallization in ethanol, 36 gr of a solid having a melting point of 195° C. are obtained, which is pyridine 2,5-dihydroxy benzene sulfonate dibenzene sulfonate.

EXAMPLE 7

A solution of 27 gr of diethylamine 2,5-dihydroxy benzene sulfonate in 150 ml of pyridine are placed in a flask provided with stirring and refrigerating means, and 19 ml of benzene sulfonyl chloride are slowly added. Stirring is continued for 24 hours, and the reaction mixture is poured on to a mixture of ice and concentrated hydrochloric acid. It is extracted with chloroform, and finally 13 gr of pyridine 2,5-dihydroxy benzene sulfonate mono-benzene sulfonate, melting at 75° C., are obtained.

EXAMPLE 8

A solution of 20 gr of diethylamine 2,5-dihydroxy benzene sulfonate in 75 ml of pyridine are placed in a flask provided with stirring and refrigerating means, and 28.5 gr of tosyl chloride are slowly added. Stirring is continued for four hours, and the reaction mixture is poured on to a mixture of ice and concentrated hydrochloric acid. It is filtered and the precipitate obtained is recrystallized in ethanol or water. 40 gr of pyridine 2,5-dihydroxy benzene sulfonate ditosylate, having a melting point of 198° C., are obtained.

EXAMPLE 9

A solution of 100 gr of diethylamine 2,5-dihydroxy benzene sulfonate in 275 ml of pyridine are placed in a flask provided with stirring and refrigerating means, and 72 gr of tosyl chloride are gradually added during 1 hour. Stirring is continued for 8 hours, and the reaction mixture is poured on to a mixture of ice and concentrated hydrochloric ac 83.2 gr of pyridine 2,5-dihydroxy benzene sulfonate mono-tosylate, having a melting point of 139° C. are obtained.

EXAMPLE 10

To a solution of 42.3 gr of pyridine 2,5-dihydroxy benzene sulfonate mono-tosylate in 75 ml of absolute ethanol, 4.0 gr of sodium hydroxide dissolved in 15 ml of water are added. A precipate is formed which is collected on a filter. 34.7 gr of sodium 2,5-dihydroxy benzene sulfonate mono-tosylate are obtained. The infrared spectrum recorded in a KBr pellet gives maxima at the following frequencies: 1415, 1365, 1200, 1090, 1030 and 835 cm$^{-1}$.

EXAMPLE 11

To a solution of 42.5 gr of pyridine 2,5-dihydroxy benzene sulfonate mono-tosylate in 75 ml of ethanol, 7.3 gr of diethylamine dissolved in 15 ml of ethanol are added. A precipitate is formed which is collected on a filter. 21 gr of diethylamine 2,5-dihydroxy benzene sulfonate mono-tosylate, having a melting point of 132° C., are obtained.

EXAMPLE 12

1.0 g of morpholine was added to a warm solution of 4.2 g of pyridine 2.5-dihydroxybenzenesulphonate monotosylate in 10 ml of ethanol. A precipitate was formed and this was collected on a filter. 3.0 g of morpholine 2.5-dihydroxybenzenesulphonate monotosylate, having a melting point of 172°-4° C., were obtained. The infra-red spectrum recorded on a KBr disc showed maxima at the following frequencies: 1595, 1360, 1250, 1150, 1005, 840 and 740 cm$^{-1}$.

EXAMPLE 13

8.0 g of piperazine hexahydrate were added to a warm solution of 17 g of pyridine 2.5-dihydroxybenzenesulphonate monotosylate in 30 ml of ethanol. A precipitate was formed and this was collected on a filter. 13 g of piperazine 2.5-dihydroxybenzenesulphonate monotosylate, having a melting point of 171°-174° C., were obtained. The infra-red spectrum recorded on a KBr disc gave maxima at the following frequencies: 3300, 1420, 1350, 1150, 1005, 905 and 750 cm$^{-1}$.

EXAMPLE 14

2.0 g of piperazine hexahydrate were added to a warm solution of 8.5 g of pyridine 2.5-dihydroxybenzenesulphonate monotosylate in 10 ml of ethanol. A precipitate was formed and this was collected on a filter. 6.9 g of piperazine bis(2.5-dihydroxybenzenesulphonate monotosylate), having a melting point of 242°-5° C., were obtained. The infra-red spectrum recorded on a KBr disc showed maxima at the following frequencies: 1595, 1420, 1370, 1180, 1020, 910, 840 and 810 cm$^{-1}$.

EXAMPLE 15

1.0 g of piperidine was added to a warm solution of 4.2 g of pyridine 2.5-dihydroxybenzenesulphonate monotosylate in 10 ml of ethanol. A precipitate was formed and this was collected on a filter. 3.9 g of piperidine 2.5-dihydroxybenzenesulphonate monotosylate, having a melting point of 170°-1° C., were obtained. The infra-red spectrum recorded on a KBr disc showed maxima at the following frequencies: 1500, 1350, 1290, 1190, 1020, 910 and 840 cm$^{-1}$.

EXAMPLE 16

An excess of diethylamine was added to a suspension of 159 g of pyridine 2.5-dihydroxybenzenesulphonate dibenzoate in 500 ml of ethanol at ambient temperature; the mixture was stirred for 3 hours and then filtered. The operation was repeated using the filtered solid material, only a little diethylamine being added and the mixture being gently heated. The mixture was allowed to cool and was filtered. 93 g of diethylamine 2.5-dihydroxybenzenesulphonate dibenzoate, having a melting point of 229° C., were obtained. The infra-red spectrum recorded on a KBr disc showed maxima at the following frequencies: 1740, 1470, 1240, 1170, 1020 and 700 cm$^{-1}$.

EXAMPLE 17

9.7 g of piperazine hexahydrate, dissolved in 20 ml of ethanol, were added to a warm solution of 24 g of pyridine 2.5-dihydroxybenzenesulphonate dibenzoate in 100 ml of ethanol. A precipitate was formed and this was collected on a filter. 21.7 g of piperazine 2.5-dihydroxybenzenesulphonate dibenzoate, having a melting point of 144°-6° C., were obtained. The infra-red spectrum recorded on a KBr disc showed maxima at the following frequencies: 3280, 1735, 1450, 1240, 1060, 1025, 860 and 710 cm$^{-1}$.

EXAMPLE 18

0.9 g of morpholine was added to a warm solution of 4.8 g of pyridine 2.5-dihydroxybenzenesulphonate dibenzoate in 15 ml of ethanol. A precipitate was formed and this was collected on a filter. 4.2 g of morpholine 2.5-dihydroxybenzenesulphonate dibenzoate, having a melting point of 212°-5° C., were obtained. The infra-red spectrum recorded on a KBr disc showed maxima at the following frequencies: 1740, 1480, 1240, 1180, 1030, 1020, 725 and 710 cm$^{-1}$.

EXAMPLE 19

0.9 g of piperidine was added to a warm solution of 4.8 g of pyridine 2.5-dihydroxybenzenesulphonate dibenzoate in 20 ml of ethanol. A precipitate was formed and this was collected on a filter. 4.3 g of piperidine 2.5-dihydroxybenzenesulphonate dibenzoate, having a melting point of 190°-3° C were obtained. The infra-red spectrum recorded on a KBr disc showed maxima at the following frequencies: 1730, 1455, 1270, 1240, 1170, 1030, 1060, 1010, 900 and 705 cm$^{-1}$.

EXAMPLE 20

9.7 g of piperazine hexahydrate were added to a warm solution of 47.7 g of pyridine 2.5-dihydroxybenzenesulphonate dibenzoate in 200 ml of ethanol. A precipitate was formed and this was collected on a filter. 44 g of piperazine bis(2.5-dihydroxybenzenesulphonate dibenzoate), having a melting point of 226° C., were obtained. The infra-red spectrum recorded on a KBr disc showed maxima at the following frequencies: 1720, 1600, 1470, 1445, 1235, 1160, 1250, 1210 and 700 cm$^{-1}$.

EXAMPLE 21

0.4 g of sodium hydroxide dissolved in a minimum quantity of water was added to a suspension of 4.8 g pyridine 2.5-dihydroxybenzenesulphonate dibenzoate in 50 ml of ethanol. The precipitate obtained in the water was recrystallized, and 2.8 g of sodium 2.5-dihydroxybenzenesulphonate dibenzoate were obtained. The infra-red spectrum recorded on a KBr disc, gave maxima at the following frequencies: 1740, 1480, 1465, 1240, 1175, 1060, 1025 and 705 cm$^{-1}$.

EXAMPLE 22

In an erlenmeyer provided with stirring and refrigeration are placed 50–60 ml of 18 N sulfuric acid, and 13.8 g of the pyridine salt of the mono-O-(p-chloro phenoxy isobutyrate) of 2,5-dihydroxy benzene sulfonic acid are added, preferably the isomer esterified in 5-position, and this is left stirring at a low temperature for 10 minutes. Then 50 ml of ethyl ether are added, and stirring is continued until the two layers are completely clear. The two layers are separated by means of a dropping funnel, and the aqueous phase is extracted with 2 × 50 ml of ethyl ether. The organic phase is dried over anhydrous sodium sulfate, filtered, and evaporated at reduced pressure at 35° C. Thus 10.1 g of mono-O-(p-chlorophenoxy isobutyrate) of 2,5-dihydroxy benzene sulfonic acid are obtained in the form of an oil, whose infrared spectrum measured on a KBr tablet gives maxima at the following frequencies: 3290, 1740, 1480, 1220, 1110, 1000, 815 and 700 cm$^{-1}$.

EXAMPLE 23

To a solution of 1.0 g of piperazine hexahydrate in 10 ml of ethanol, a solution of 1.9 g of mono-O-(p-chloro phenoxy isobutyrate) of 2,5-dihydroxy benzene sulfonic acid, obtained according to Example 22, in 10 ml of ethanol, is added. The precipitate formed is filtered, and 2.1 g of the mono-salt of piperazine of mono-O-(p-chloro phenoxy isobutyrate) of 2,5-dihydroxy benzene sulfonic acid are obtained, in crystalline form having a melting point of 202°–205° C.

EXAMPLE 24

To a solution of 1.9 g of piperazine hexahydrate in 20 ml of ethanol, a solution of 7.5 g of mono-O-(p-chloro phenoxy isobutyrate) of 2,5-dihydroxy benzene sulfonic acid, obtained according to Example 22, in 20 ml of ethanol, is added. The precipitate formed is filtered, and 9.2 g of the di-salt of piperazine of mono-O-(p-chloro phenoxy isobutyrate) of 2,5-dihydroxy benzene sulfonic acid are obtained, in crystalline form, having a melting point of 245°–246° C.

EXAMPLE 25

To a solution of 3.8 g of mono-O-(p-chloro phenoxy isobutyrate) of 2,5-dihydroxy benzene sulfonic acid, obtained according to Example 22 in 15 ml of a 5:1 mixture (v/v) of ethanol and water, a slight excess of calcium carbonate is added. This is filtered and evaporated, and 3.8 g of the calcium salt of mono-O-(p-chloro phenoxy isobutyrate) of 2,5-dihydroxy benzene sulfonic acid are obtained in the form of a white powder whose infrared spectrum determined in a KBr tablet gives maxima at the following frequencies: 3480, 3180, 1770, 1750, 1490, 1220, 860 and 820 cm$^{-1}$.

EXAMPLE 26

To a solution of 3.8 g of mono-O-(p-chloro phenoxy butyrate) of 2,5-dihydroxy benzene sulfonic acid, obtained according to Example 22, in 15 ml of ethanol, a slight excess of basic magnesium carbonate is added. This is filtered, evaporated and 3.0 g of the magnesium salt of mono-O-(p-chloro phenoxy isobutyrate) of 2,5-dihydroxy benzene sulfonic acid are obtained in the form of a slightly hygroscopic white powder, having an infrared spectrum measured in a KBr tablet which has maxima at the following frequencies: 3390, 1750, 1480, 1230, 1170, 1020, 820 and 700 cm$^{-1}$.

EXAMPLE 27

To a solution of 263 g of diethylamine 2,5-dihydroxy benzene sulfonate in 500 ml of pyridine, 470 g of the chloride of p-chloro phenoxy isobutyric acid are added with stirring. The reaction is exothermic, but it is effected without refrigeration, letting it cool to ambiant temperature. A coloured precipitate forms, which is filtered and washed with water, and then copiously with ethanol. Thus 601 g of the pyridine salt of the di-O-(p-chloro phenoxy isobutyrate) of 2,5-dihydroxy benzene sulfonic acid are obtained in the form of a white crystalline powder having a melting point of 186°–188° C.

EXAMPLE 28

In an erlenmeyer provided with stirring and refrigeration, 50–60 ml of 18 N sulfuric acid are placed, 19,8 g of the pyridine salt of di-O-(p-chloro phenoxy isobutyrate) of 2,5-dihydroxy benzene sulfonic acid are added, and this is left stirring, at a low temperature, for 20 minutes. Then 50 ml of ethyl ether are added, and stirring is continued until the two layers are completely transparent. The two layers are separated in a dropping funnel, and the aqueous phase is extracted with 2 × 50 ml of ethyl ether. The organic phase is dried over anhydrous sodium sulfate, filtered, evaporated under reduced pressure, and 17.5 g of di-O-(p-chlorophenoxy isobutyrate) of 2,5-dihydroxy benzene sulfonic acid are obtained in the form of a viscous oil whose infrared spectra give maxima at the following frequencies: 3285, 2990, 1750, 1480, 1220, 1080, 1000, 820 and 705 cm$^{-1}$.

EXAMPLE 29

To a solution of 1.9 g of piperazine hexahydrate in 20 ml of ethanol, a solution of 6.0 g of di-O-(p-chlorophenoxyisobutyrate) of 2,5-dihydroxy benzene sulfonic acid obtained according to Example 28 in 10 ml of ethanol is added. The mixture is left in a refrigerator for 2 h, it is filtered, the product formed is recrystallized, and 4.3 g of the piperazine mono-salt of di-O-(p-chlorophenoxy isobutyrate) of 2,5-dihydroxy benzene sulfonic acid is obtained in the form of white crystals having a melting point of 168° C.

EXAMPLE 30

To a solution of 1.9 g of piperazine hexahydrate in 20 ml of ethanol, a solution of 12 g of di-O-(p-chlorophenoxy isobutyrate) of 2,5-dihydroxy benzene sulfonic acid obtained according to example 28 in 20 ml of ethanol is added. The precipitate formed is filtered, recrystallized and 9.8 g of the piperazine di-salt of di-O-(p-chlorophenoxy isobutyrate) of 2,5-dihydroxy benzene sulfonic acid is obtained in the form of white crystals having a melting point of 197°–200° C.

EXAMPLE 31

To a solution of 6.0 g of di-O-(p-chloro phenoxy isobutyrate) of 2,5-dihydroxy benzene sulfonic acid obtained according to Example 28 in 20 ml of ethanol, an excess of calcium carbonate is added, this is filtered, evaporated and 5.9 g of the calcium salt of di-O-(p-chlorophenoxy isobutyrate) of 2,5-dihydroxy benzene sulfonic acid is obtained in the form of white crystals whose infrared spectrum, measured on a KBr tablet, gives maxima at the following frequencies: 3520, 3400, 1750, 1480, 1230, 1080, 820 and 700 cm$^{-1}$.

EXAMPLE 32

To a solution of 6.0 g of di-O-(p-chloro phenoxy isobutyrate) of 2,5-dihydroxy benzene sulfonic acid obtained according to Example 28 in 20 ml of ethanol, a slight excess of basic magnesium carbonate is added, this is filtered, evaporated and 5.0 g of magnesium salt of di-O-(p-chloro phenoxy isobutyrate) of 2,5-dihydroxy benzene sulfonic acid is obtained in the form of a white powder whose infrared spectrum, measured in a KBr tablet, gives maxima at the following frequencies: 3400, 1760, 1650, 1480, 1230, 1090, 1020, 840, 820 and 705 cm$^{-1}$.

EXAMPLE 33

To a solution of 10.70 g (0.025 mole) of calcium 2,5-dihydroxy benzene sulfonate (containing 0.63 equivalents of H$_2$O) in 100 ml of acetone containing 4.5 ml of water, 20.55 g (0.050 mole) of p-chloro phenoxy isobutyric acid anhydride are added, and with stirring for 4 hours, 1.4 g (0.025 mole) of CaO are added portionswise (Ca content determined previously). A precipitate of calcium p-chloro phenoxy isobutyrate dihydrate forms gradually. After 5 hours reaction at room temperature, this is concentrated to dryness under reduced pressure, the amorphous residue is taken up in 200 ml of water at 2° C., it is left at this temperature for 2 hours, and then 12.0 g of calcium p-chloro phenoxy isobutyrate dihydrate is filtered off. The mother liquors are concentrated to dryness, under reduced pressure, and the amorpho - crystalline residue is crystallized with ether. The fraction thus obtained is soluble in tetrahydrofuran (THF), ethyl acetate acetone. It is recrystallized in the THF solution with ether.

The product crystallized with one molecule of the solvent, e.g. THF, acetone, ethyl acetate. The crystallization solvent is removed at 100° C., 17 hours. Yield: 15.5 g (74%). The product, which exhibits polymorphism, is calcium 2-O-(p-chlorophenoxy isobutyryl) 2,5-dihydroxy benzene sulfonate. Coefficients of molecular extinction in UV:

$$\left. \begin{array}{l} \epsilon\ 223\ nm\ =\ 39,500 \\ \epsilon\ 280\ nm\ =\ \phantom{0}8,500 \end{array} \right\} s = H_2O$$

The infrared spectrum, measured with nujol, gives maxima at 3340, 1750, 1600, 1230, 1200, 1130, 1090, 1030, 870, 830 and 720 cm$^{-1}$.

EXAMPLE 34

To an aqueous solution of 93.48 g (0.11 mole) of calcium 2-O-(p-chloro phenoxy isobutyryl) 2,5-dihydroxy benzene sulfonate dihydrate, 110 ml of 2N sulfuric acid are added dropwise, with stirring; the suspension is cooled to 2° C. for 120 minutes, SO$_4$Ca is removed by filtering. To the clear filtrate 4.76 g (0.11 mole) of MgO are added with stirring. After a few minutes, the whole of the oxide was consumed. The solvent is removed under reduced pressure, and the amorphous residue is taken up in acetone. The remaining SO$_4$Ca is filtered, the solvent is removed under reduced pressure, the evaporation residue is taken up in ether, wherefrom 91.0 g of magnesium 2-O-(p-chlorophenoxy isobutyryl) 2,5-dihydroxy benzene sulfonate crystallizes. This product is kept at 98° C. for 17 hours. At room temperature, the ester re-equilibrates its H$_2$O content. 83.8 g of magnesium 2-O-(p-chlorophenoxy isobutyryl) 2,5-dihydroxybenzene sulfonate dihydrate are obtained.

The infrared spectrum, measured with nujol, gives maxima at 3450, 1750, 1600, 1200, 1090, 1040, 1030, 970, 870, 840 and 720 cm$^{-1}$.

EXAMPLE 35

To a solution of 1.694 g (2 mmoles) of calcium 2-O-(p-chlorophenoxy isobutyryl) 2,5-dihydroxy benzene sulfonate in water, 2 ml of 2N sulfuric acid are added, the SO$_4$Ca formed is removed by filtration, 172.2 mg (2 mmoles) of piperazine are added to the filtrate. This is evaporated to dryness under reduced pressure; the residue is taken up in acetone, a small amount of residual SO$_4$Ca is removed by filtration, the filtrate is evaporated to dryness, and the piperazine salt is crystallized in ethyl acetate, and recrystallized in a mixture of tetrahydrofuran and ether. Bis-2-O-(p-chlorophenoxy isobutyryl)-2,5-dihydroxy benzene sulfonate of piperazine having a melting point of 226°-229° C. is obtained.

Because of the low toxicity of these compounds, and hence their high therapeutical index, their clinical performance is shown to be extremely interesting for the treatment of various types of hyperlipemia and dislipemia.

The pharmacodynamical properties of the compounds according to the invention are illustrated in the Table VI herebelow e.g. the medium lethal dose (LD$_{50}$), and the percent inhibition with respect to Triton WR-1339 of total cholesterol, triglycerides and total lipids. In this Triton WR-1339 method, all the compounds are administered at a dose of 2 mMoles/Kg orally excepted those compounds in which is the residue of p-chlorophenoxy isobutyric acid, which are administered orally at a dose corresponding to 2 mMoles of R per Kg, i.e. the amount used is calculated on the basis of the residue R only.

Table VI

| | Percentage reduction of lipids | | | LD$_{50}$ |
|---|---|---|---|---|
| | Cholesterol | Triglycerides | Total Lipids | (mg/kg) |
| pyridine 2,5-dihydroxybenzenesulfonate mono-p-chloro phenoxy isobutyrate | 16 | 27 | 23 | 900 |
| pyridine 2,5-dihydroxybenzenesulfonate mononicotinate | 17 | 24 | 25 | 1.000 |
| pyridine 2,5-dihydroxybenzenesulfonate ditosylate | 17 | 44 | 31 | 700 |
| pyridine 2,5-dihydroxybenzenesulfonate monotosylate | 18 | 36 | 27 | 680 |
| sodium 2,5-dihydroxybenzenesulfonate monotosylate | 10 | 36 | 39 | 3.623 |
| diethylamine 2,5-dihydroxybenzenesulfonate monotosylate | 23 | 32 | 31 | 6.588 |
| morpholine 2,5-dihydroxybenzenesulfonate monotosylate | 12 | 23 | 31 | 5.301 |
| piperazine 2,5-dihydroxybenzenesulfonate monotosylate | 18 | 43 | 42 | 10.750 |
| piperazine bis(2,5-dihydroxybenzenesulfonate monotosylate | 11 | 25 | 17 | 6.000 |
| piperidine bis(2,5-dihydroxybenzenesulfonate monotosylate) | 15 | 26 | 33 | 5.000 |
| diethylamine 2,5-dihydroxybenzenesulfonate dibenzoate | 12 | 14 | 22 | 14.160 |
| piperazine 2,5-dihydroxybenzenesulfonate dibenzoate | 13 | 18 | 20 | 5.500 |
| morpholine 2,5-dihydroxybenzenesulfonate dibenzoate | 12 | 17 | 21 | 4.000 |
| piperidine 2,5-dihydroxybenzenesulfonate dibenzoate | 14 | 19 | 23 | 2.000 |
| piperazine bis(2,5-dihydroxybenzene sulfonate dibenzoate) | 9 | 14 | 16 | 8.000 |
| sodium 2,5-dihydroxybenzenesulfonate dibenzoate | 12 | 17 | 20 | 6.315 |
| mono-salt of piperazine of mono-O-(p-chloro phenoxy isobutyrate) of 2,5-dihydroxybenzenesulfonic acid | 9 | 49 | 25 | 4.300 |
| di-salt of piperazine of mono-O-(p-chloro phenoxy | | | | |

Table VI-continued

| | Percentage reduction of lipids | | | $LD_{50}$ (mg/kg) |
|---|---|---|---|---|
| | Cholesterol | Triglycerides | Total Lipids | |
| isobutyrate) of 2,5-dihydroxybenzenesulfonic acid | 16 | 31 | 26 | 4.700 |
| calcium salt of mono-O-(p-chloro phenoxy isobutyrate) of 2,5-dihydroxybenzenesulfonic acid | 27 | 40 | 26 | 4.500 |
| magnesium salt of mono-O-(p-chloro phenoxy isobutyrate) of 2,5-dihydroxybenzenesulfonic acid | 19 | 44 | 28 | 3.100 |
| pyridine salt of di-O-(p-chloro phenoxy isobutyrate) of 2,5-dihydroxybenzenesulfonic acid | 20 | 32 | 31 | 1.100 |
| piperazine mono-salt of di-O-(p-chloro phenoxy isobutyrate) of 2,5-dihydroxybenzenesulfonic acid | 25 | 49 | 28 | 11.000 |
| piperazine di-salt of di-O-(p-chloro phenoxy isobutyrate) of 2,5-dihydroxybenzenesulfonic acid | 29 | 21 | 37 | 8.000 |
| calcium salt of di-O-(p-chloro phenoxy isobutyrate) of 2,5-dihydroxybenzenesulfonic acid | 27 | 33 | 29 | 6.000 |
| magnesium salt of di-O-(p-chlorophenoxy isobutyrate) of 2,5-dihydroxybenzene sulfonic acid | 5 | 51 | 25 | 4.780 |
| calcium 2-O-(p-chloro phenoxy isobutyryl)-2,5-dihydroxybenzenesulfonate | 30 | 32 | 26 | 3.350 |
| magnesium 2-O-(p-chloro phenoxy isobutyryl)-2,5-dihydroxybenzenesulfonate | 18 | 21 | 27 | 2.450 |

The proposed human dose is 1 to 3 gr. per day for all compounds. The preferred pharmaceutical formulations are tablets and capsules, containing 250 or 500 mg of active compound of formula I, II or III per unit dose.

| Example of formulation for a tablet | |
|---|---|
| piperazine 2,5-dihydroxybenzenesulfonate monotosylate | 0.500 g |
| rice starch | 0.100 g |
| lactose | 0.100 g |
| polyvinylpyrrolidone | 0.020 g |
| magnesium stearate | 0.003 g |
| weight of tablet | 0.723 g |

| Example of formulation for a capsule | |
|---|---|
| piperazine 2,5-dihydroxybenzenesulfonate monotosylate | 0.250 g |
| lactose | 0.050 g |
| aerosil | 0.001 g |
| magnesium stearate | 0.002 g |
| weight of capsule | 0.303 g |

I claim:

1. Diethylamine 2,5-dihydroxy benzene sulfonate monotosylate.

2. Morpholine 2,5-dihydroxy benzene sulfonate monotosylate.

* * * * *